United States Patent
King et al.

(10) Patent No.: US 11,191,632 B2
(45) Date of Patent: Dec. 7, 2021

(54) TEMPORARY DIAMETER REDUCTION CONSTRAINT ARRANGEMENT FOR A STENT GRAFT IN COMBINATION WITH A STENT GRAFT

(71) Applicant: Cook Medical Technologies LLC, Bloomington, IN (US)

(72) Inventors: Chantelle King, Woodridge (AU); Logan Smith, Mount Gravatt (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 15/347,907

(22) Filed: Nov. 10, 2016

(65) Prior Publication Data
US 2018/0125634 A1 May 10, 2018

(51) Int. Cl.
*A61F 2/07* (2013.01)
*A61F 2/95* (2013.01)
*A61F 2/89* (2013.01)
*A61F 2/06* (2013.01)

(52) U.S. Cl.
CPC .............. *A61F 2/07* (2013.01); *A61F 2/95* (2013.01); *A61F 2/89* (2013.01); *A61F 2002/061* (2013.01); *A61F 2002/9511* (2013.01); *A61F 2220/0075* (2013.01)

(58) Field of Classification Search
CPC .............................................. A61F 2002/9511
See application file for complete search history.

(56) References Cited

U.S. PATENT DOCUMENTS

| | | |
|---|---|---|
| 4,902,508 A | 2/1990 | Badylak et al. |
| 5,554,389 A | 9/1996 | Badylak et al. |
| 5,993,844 A | 11/1999 | Abraham et al. |
| 6,099,567 A | 8/2000 | Badylak et al. |
| 6,206,931 B1 | 3/2001 | Cook et al. |
| 6,635,080 B1 | 10/2003 | Lauterjung |
| 7,252,680 B2 * | 8/2007 | Freitag .................. A61F 2/88 606/108 |
| 7,407,509 B2 | 8/2008 | Greenberg et al. |
| 8,926,686 B2 | 1/2015 | King |

(Continued)

FOREIGN PATENT DOCUMENTS

| | | |
|---|---|---|
| JP | 2005304792 A | 11/2005 |
| WO | 9853761 | 12/1998 |

*Primary Examiner* — Martin T Ton
(74) *Attorney, Agent, or Firm* — Crowell & Moring

(57) ABSTRACT

A temporary diameter reduction constraint arrangement for a stent graft in combination with a stent graft is disclosed. The stent graft has a proximal end and a distal end and comprises a biocompatible graft material tube and a plurality of longitudinally spaced apart self-expanding stents fastened thereto, including at least an end stent and a plurality of intermediate stents. The constraint arrangement comprises: an elongate receiver extending longitudinally within the graft material tube; a first wire extending longitudinally along the graft material tube in a first serpentine pattern; and a second wire extending longitudinally along the graft material tube in a second serpentine pattern, wherein at least one of the first and second wires repeatedly loops over the receiver along a longitudinal length of the stent graft thereby securing the stent graft to the receiver. In one embodiment there is also a plurality of loops of thread to reduce the stent graft.

33 Claims, 11 Drawing Sheets

(56) References Cited

U.S. PATENT DOCUMENTS

| | | |
|---|---|---|
| 8,968,384 B2 | 3/2015 | Pearson et al. |
| 9,504,555 B2 | 11/2016 | Hartley et al. |
| 2009/0171451 A1 | 7/2009 | Kuppurathanam et al. |
| 2013/0116773 A1 | 5/2013 | Roeder et al. |
| 2014/0148895 A1* | 5/2014 | King .................. A61F 2/07 |
| | | 623/1.13 |

* cited by examiner

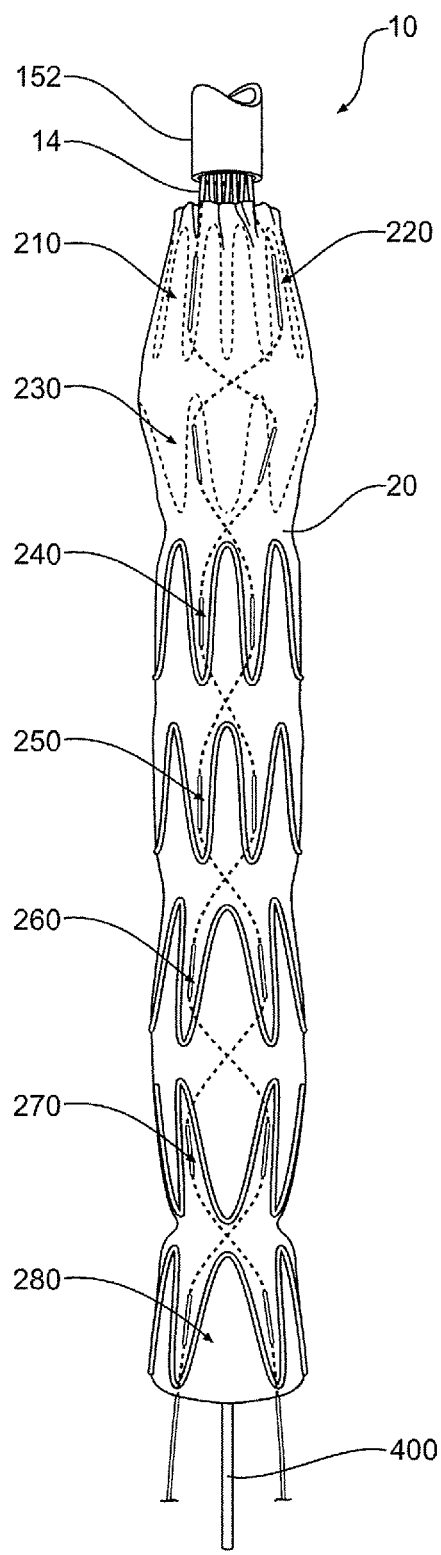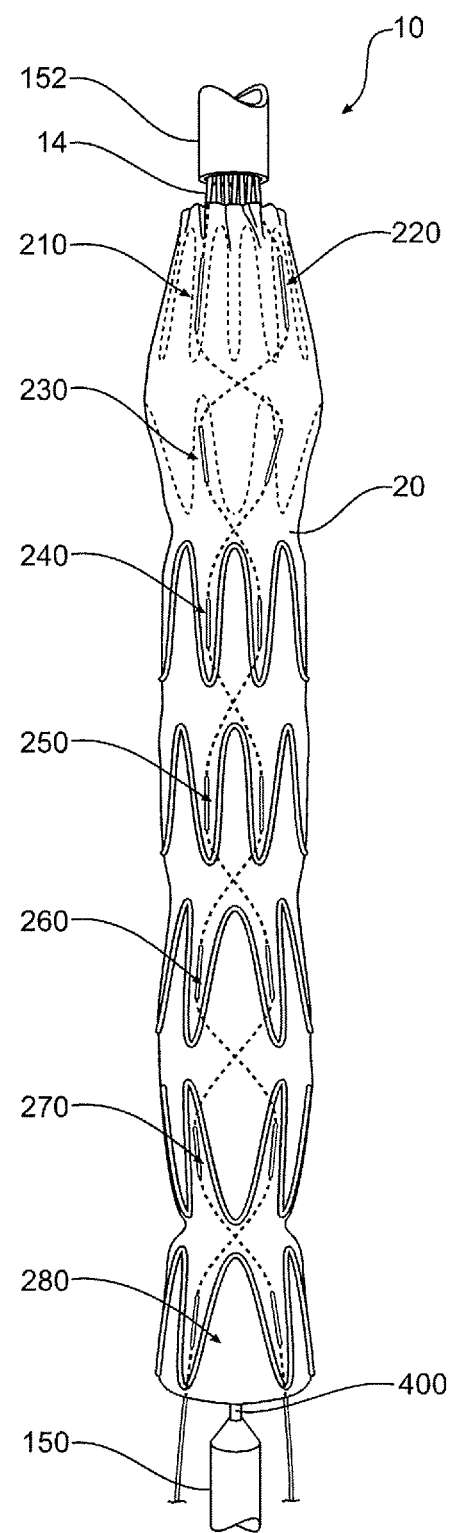
*Figure 6B*  *Figure 6C*

# TEMPORARY DIAMETER REDUCTION CONSTRAINT ARRANGEMENT FOR A STENT GRAFT IN COMBINATION WITH A STENT GRAFT

This invention relates to medical devices and more particularly to stent grafts mountable onto a deployment device for endovascular introduction.

BACKGROUND OF THE INVENTION

This invention will be particularly discussed in relation to stent grafts for placement into the thoracic abdominal aorta or into the abdominal aorta for the treatment of aneurysms. The invention, however, is not so restricted and may be applied to stent grafts for placement in any lumen of the human or animal body.

The positioning of stent grafts is very important for a number of reasons, including in many cases the need to avoid occlusion of branch arteries. Positioning is complicated however because the diameter of a stent graft is deliberately made larger than the diameter into which it is to be placed to allow for accurate sealing against the vessel wall, possible errors in sizing and subsequent relaxation of the vessel wall.

Once released from a delivery device, a stent graft with self-expanding stents will take up a position against the vessel wall and it will be difficult if not impossible to reposition it. This can be dangerous if, for instance, renal arteries are occluded.

Stent graft assemblies with diameter reducing ties have been developed to assist surgeons with the task of positioning stent grafts after initial release from a deployment device. Sewing and positioning of such ties during manufacture can be difficult and time consuming. Furthermore, errors in this process can have adverse effects.

It is an object of the invention to address difficulties described above while at the same time improving safety and simplifying assembly or to at least provide a useful alternative assembly technique.

Throughout this specification the term distal with respect to a portion of the aorta, a deployment device or a prosthesis is the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

According to a first aspect of the invention, there is provided a temporary diameter reduction constraint arrangement for a stent graft in combination with a stent graft, the stent graft having a proximal end and a distal end and comprising a biocompatible graft material tube and a plurality of longitudinally spaced apart self-expanding stents fastened thereto, including at least an end stent and a plurality of intermediate stents, the constraint arrangement comprising:

an elongate receiver extending longitudinally within the graft material tube;

a first wire extending longitudinally along the graft material tube in a first serpentine pattern; and a second wire extending longitudinally along the graft material tube in a second serpentine pattern, wherein at least one of the first and second wires repeatedly loops over the receiver along a longitudinal length of the stent graft thereby securing the stent graft to the receiver.

In one form, the first and second serpentine patterns cross each other in a criss-cross lacing pattern.

In one form, the first and second wires repeatedly cross each other within the graft material tube.

In one form, the first and second wires lie predominately inside the graft material tube.

In one form, the first and second wires repeatedly penetrate a tubular wall of the graft material tube from inside the graft material tube to outside the graft material tube and then penetrate the tubular wall back from outside the graft material tube to inside the graft material tube, thereby forming a plurality of external wire portions.

In one form, each intermediate stent is a zig-zag stent comprising struts and bends forming peaks and valleys and wherein the intermediate stents are longitudinally spaced apart such that their respective peaks are substantially longitudinally aligned.

In one form, the external wire portions are disposed within a V, or an inverted V, formed between adjacent struts of one of the plurality of intermediate stents.

In one form, the receiver is a temporary loading member, the temporary member provided to facilitate loading of the constraint arrangement onto a guide wire cannula.

In one form, the temporary loading member comprises a tube having a through-bore.

In one form, the receiver is a guide wire cannula.

According to a second aspect of the invention, there is provided a temporary diameter reduction constraint arrangement for a stent graft in combination with a stent graft, the stent graft having a proximal end and a distal end and comprising a biocompatible graft material tube and a plurality of longitudinally spaced apart self-expanding stents fastened thereto, including at least an end stent and a plurality of intermediate stents, the constraint arrangement comprising:

an elongate receiver extending longitudinally within the graft material tube;

a first wire extending longitudinally along the graft material tube in a first serpentine pattern;

a second wire extending longitudinally along the graft material tube in a second serpentine pattern; and a plurality of loops of thread, each loop engaged with one or other of the first and second wires and engaged around a portion of the stent graft circumferentially spaced a selected distance away from its wire, and drawn tight and tied to itself to reduce the stent graft, wherein at least one of the first and second wires repeatedly loops over the receiver along a longitudinal length of the stent graft thereby securing the stent graft to the receiver.

In one form, the first and second serpentine patterns cross each other in a criss-cross lacing pattern.

In one form, the first and second wires repeatedly cross each other within the graft material tube.

In one form, the first and second wires lie predominately inside the graft material tube.

In one form, the first and second wires repeatedly penetrate a tubular wall of the graft material tube from inside the graft material tube to outside the graft material tube and then penetrate the tubular wall back from outside the graft material tube to inside the graft material tube, thereby forming a plurality of external wire portions.

In one form, each intermediate stent is a zig-zag stent comprising struts and bends forming peaks and valleys and wherein the intermediate stents are longitudinally spaced apart such that their respective peaks are substantially longitudinally aligned.

In one form, the external wire portions are disposed within a V, or an inverted V, formed between adjacent struts of one of the plurality of intermediate stents.

In one form, the receiver is a temporary loading member, the temporary member provided to facilitate loading of the constraint arrangement onto a guide wire cannula.

In one form, the temporary loading member comprises a tube having a through-bore.

In one form, the receiver is a guide wire cannula.

According to a third aspect of the invention, there is provided a temporary diameter reduction constraint arrangement for a stent graft in combination with a stent graft, the stent graft having a proximal end and a distal end and comprising a biocompatible graft material tube and a plurality of longitudinally spaced apart self-expanding stents fastened thereto, including at least an end stent and a plurality of intermediate stents, each intermediate stent being a zig-zag stent comprising struts and bends forming peaks and valleys, the intermediate stents longitudinally spaced apart such that their respective peaks are substantially longitudinally aligned, the constraint arrangement comprising:

an elongate receiver extending longitudinally within the graft material tube, the receiver comprising a tube having a through-bore;

a first wire extending longitudinally along the graft material tube in a first serpentine pattern;

a second wire extending longitudinally along the graft material tube in a second serpentine pattern, the first and second serpentine patterns crossing each other in a criss-cross lacing pattern; and a plurality of loops of thread, each loop engaged with one or other of the first and second wires and engaged around a portion of the stent graft circumferentially spaced a selected distance away from its wire, and drawn tight and tied to itself to reduce the stent graft, wherein at least one of the first and second wires repeatedly loops over the receiver along a longitudinal length of the stent graft thereby securing the stent graft to the receiver, the first and second wires repeatedly crossing each other within the graft material tube and the first and second wires lying predominately inside the graft material tube, and wherein the first and second wires repeatedly penetrate a tubular wall of the graft material tube from inside the graft material tube to outside the graft material tube and then penetrate the tubular wall back from outside the graft material tube to inside the graft material tube, thereby forming a plurality of external wire portions, the external wire portions disposed within a V, or an inverted V, formed between adjacent struts of one of the plurality of intermediate stents.

A detailed description of one or more embodiments of the invention is provided below along with accompanying figures that illustrate by way of example the principles of the invention. While the invention is described in connection with such embodiments, it should be understood that the invention is not limited to any embodiment. On the contrary, the scope of the invention is limited only by the appended claims and the invention encompasses numerous alternatives, modifications and equivalents. For the purpose of example, numerous specific details are set forth in the following description in order to provide a thorough understanding of the present invention.

The present invention may be practiced according to the claims without some or all of these specific details. For the purpose of clarity, technical material that is known in the technical fields related to the invention has not been described in detail so that the present invention is not unnecessarily obscured.

BRIEF DESCRIPTION OF THE DRAWINGS

This then generally describes the invention but, to assist with understanding, reference will now be made to the accompanying drawings which show preferred embodiments of the invention.

FIGS. 6A to 6C show an embodiment of the invention as part of a delivery device;

DESCRIPTION OF PREFERRED EMBODIMENTS

Figure 1:
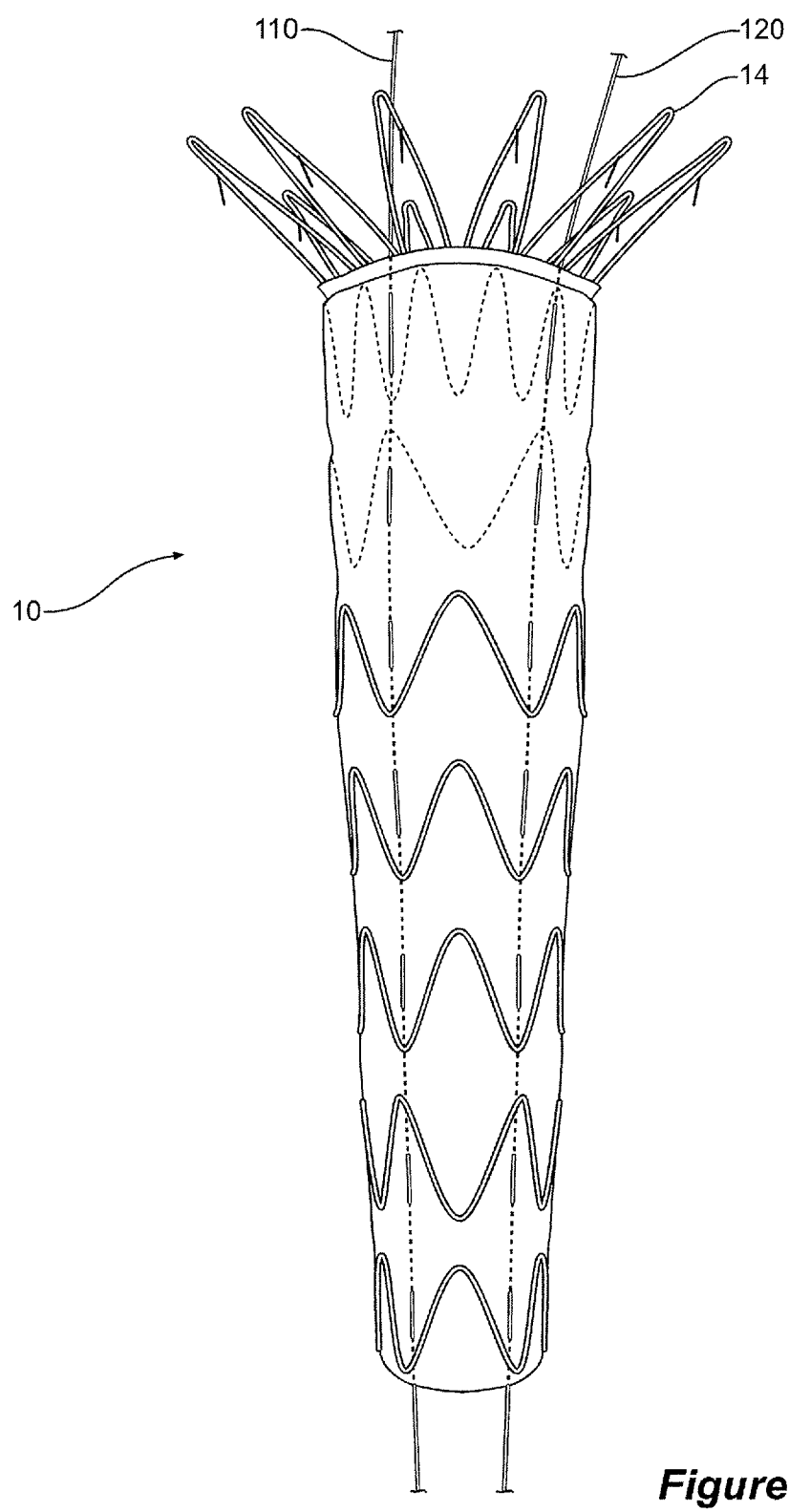
FIG. 1 shows a stent graft according to the prior art.

Referring to FIG. 1, a stent graft of the type shown in U.S. patent application Ser. No. 11/507,115 titled "Assembly of Stent Grafts" is shown. This stent graft 10 has release wires 110 and 120 that can be used together with reducing ties to achieve a reduction in the circumference of the stent graft 10 as is explained in the specification of the aforementioned U.S. patent application Ser. No. 11/507,115 titled "Assembly of Stent Grafts" which is hereby incorporated in its entirety into this specification.

A temporary diameter reduction constraint arrangement for a stent graft in combination with a stent graft is shown and described in U.S. patent application Ser. No. 13/795,088, titled "Assembly of stent grafts with diameter reducing ties" and is also hereby incorporated in its entirety into this specification.

Figure 2:
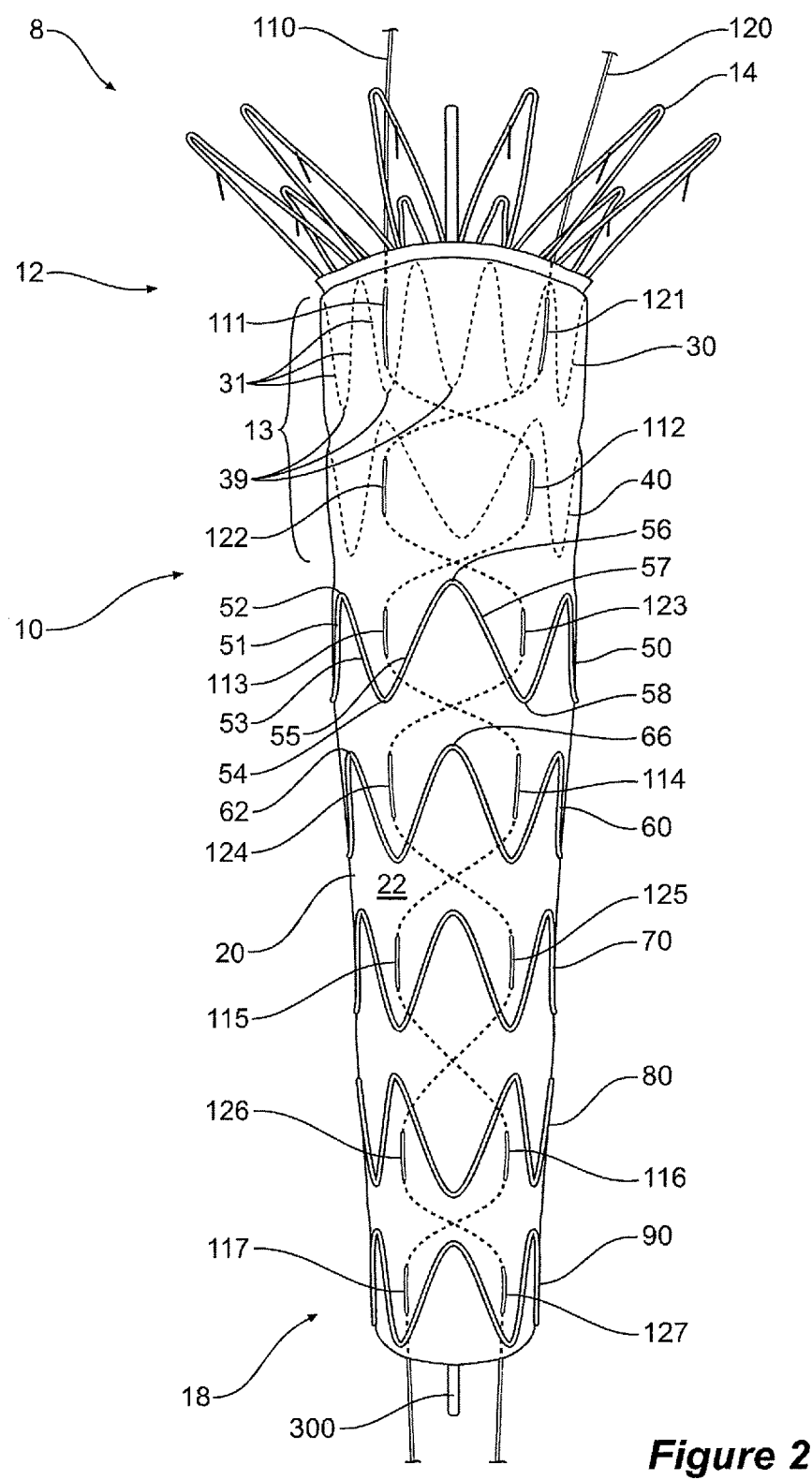
FIG. 2 is a perspective view of a temporary diameter reduction constraint arrangement for a stent graft in combination with a stent graft according to a first embodiment of the invention.

Referring to FIG. 2, a temporary diameter reduction constraint arrangement 8 for a stent graft 10 in combination with a stent graft 10 according to a first embodiment of the invention is shown. The stent graft 10 has a proximal end 12 and a distal end 18 and comprises a biocompatible graft material tube 20 of a selected diameter. It also has a plurality of longitudinally spaced apart self-expanding stents fastened thereto, including at least an end stent and a plurality of intermediate stents. More specifically, the embodiment's stent graft has two internal stents 30, 40 shown in dotted lines and a plurality of external stents 50, 60, 70, 80, 90 along the length of its tubular body, the stents 40, 50, 60, 70 and 80 being intermediate stents and the stents 30 and 90 being end stents. The internal stents 30, 40 are at the proximal end 12 and act on a sealing zone 13 also at the proximal end 12.

Preferably, the graft tube material 20 may be formed from a biocompatible material that is substantially non-toxic in the in vivo environment of its intended use and substantially unrejected by the patient's physiological system (i.e., is non-antigenic). For example, the graft tube material 20 may be made of an expanded polytetrafluoroethylene (ePTFE), polytetrafluoroethylene, silicone, polyurethane, polyamide (nylon), polyethylene, polypropylene, polyaramids, polyacrylonitrile, cellulose, or another flexible biocompatible material. The graft tube material 20 also may be made of known fabric graft materials, e.g., woven polyester such as DACRON® from Invista (Wichita, Kans.), polyetherurethanes such as THORALON® from Thoratec Corporation (Pleasanton, Calif.), or polyethylene such as an ultra-high molecular weight polyethylene (UHMwPE) such as DYNEEMA® from DSM Dyneema LLC (Stanley, N.C.). In addition, materials that are not inherently biocompatible may be subjected to surface modifications to render the materials biocompatible. Examples of surface modifications include, for example, graft polymerization of biocompatible polymers on the surface, coating of the surface with a crosslinked biocompatible polymer, chemical modification with biocompatible functional groups, or immobilization of a compatibilizing agent such as heparin or other biocompatible substances. Thus, any fibrous material having sufficient strength to survive in the in vivo environment may be used to form a textile graft, provided the final textile is biocompatible.

The graft tube material 20 material also may include a bioremodelable material such as reconstituted or naturally-derived collagenous materials. Suitable remodelable materials can be provided by collagenous extracellular matrix (ECM) materials possessing biotropic properties. For example, suitable collagenous materials may include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes may include, for instance, intestinal submucosa including small intestinal submucosa, stomach submucosa, urinary bladder submucosa, and uterine submucosa. Collagenous matrices including submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to some of the materials useful in the present invention, and their isolation and treatment, reference can be made, for example, to U.S. Pat. Nos. 4,902,508, 5,554,389, 5,993,844, 6,206,931, and 6,099,567. Non-limiting example of suitable remodelable materials may include SURGISIS® BIODESIGN™ from Cook Medical (Bloomington, Ind.) or the graft prosthesis material described in U.S. Pat. No. 6,206,931 to Cook et al., which is incorporated herein by reference in its entirety. The graft tube material also may be made of any of the materials described in U.S. Pat. No. 7,407,509 to Greenberg et al. or U.S. Patent Application Pub. No. 2009/0171451 to Kuppurathanam et al., which are incorporated herein by reference in their entirety.

Figure 3:
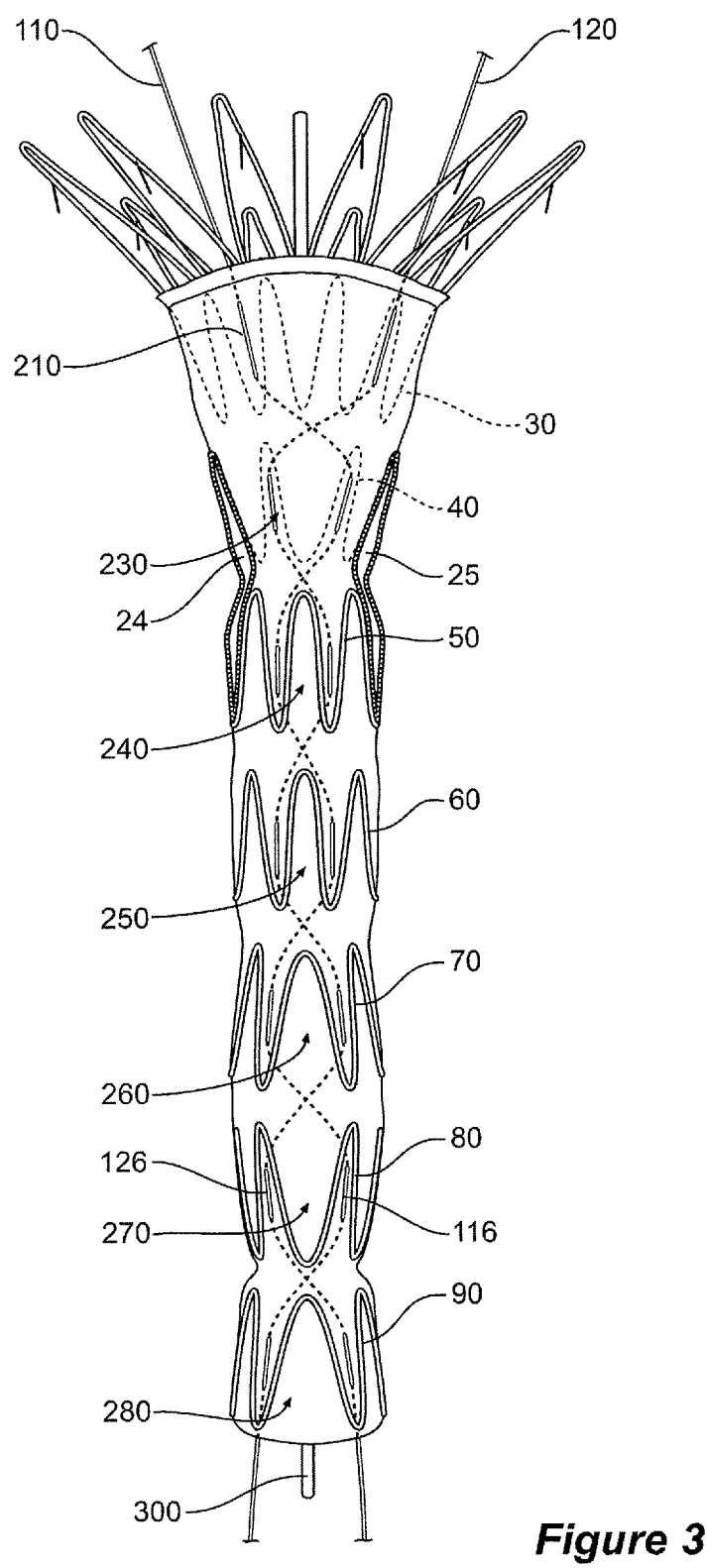
FIG. 3 is a similar view to that of FIG. 2, but shows the constraint arrangement in a partially reduced configuration.

FIG. 3 is a similar view to that of FIG. 2, but shows the constraint arrangement in a reduced condition in which the diameter is reduced. This view also shows optional fenestrations 24 and 25 which can be provided for allowing access to the renal arteries. Embodiments of the invention can facilitate matching such fenestrations 24 and 25 up with the renal arteries when the stent graft is deployed into an aorta. Methods of deployment of such a stent graft are described in PCT Patent Publication Number WO98/53761 entitled "A Prosthesis and a Method of Deploying a Prosthesis". These features and other features disclosed in PCT Patent Publication Number WO98/53761 could be used with the present invention and the disclosure of PCT Patent Publication Number WO98/53761 is herewith incorporated in its entirety into this specification.

Although the stent graft 10 shown is useable in aortas in the region of the renal arteries, the invention may be embodied in other stent grafts, which may or may not have fenestrations.

The constraint arrangement shown in FIGS. 2 and 3 comprises an elongated receiver 300 extending longitudinal within the graft material tube 20. This elongated receiver 300 is more clearly shown in FIG. 4. In this embodiment, the elongate receiver 300 is a tube with a through-bore in the form of an internal bore 310.

The constraint arrangement further comprises a first wire 110 extending longitudinal along the graft material tube 20 in a first serpentine pattern, and a second wire 120 extending longitudinally along the graft material tube 20 in a second serpentine pattern. At least one of the first and second wires 110,120 repeatedly loops over the receiver 300 along a longitudinal length of the stent graft 10 thereby securing the stent graft 10 to the receiver 300.

Referring again to FIGS. 2 and 4, it can be seen that the first and second serpentine patterns cross each other in a criss-cross lacing pattern. It can also be seen in FIG. 4 that the first and second wires 110,120 repeatedly cross each other within the graft tube material 20. The first and second wires 110,120 lie predominantly inside the graft material tube 20.

Figure 4:
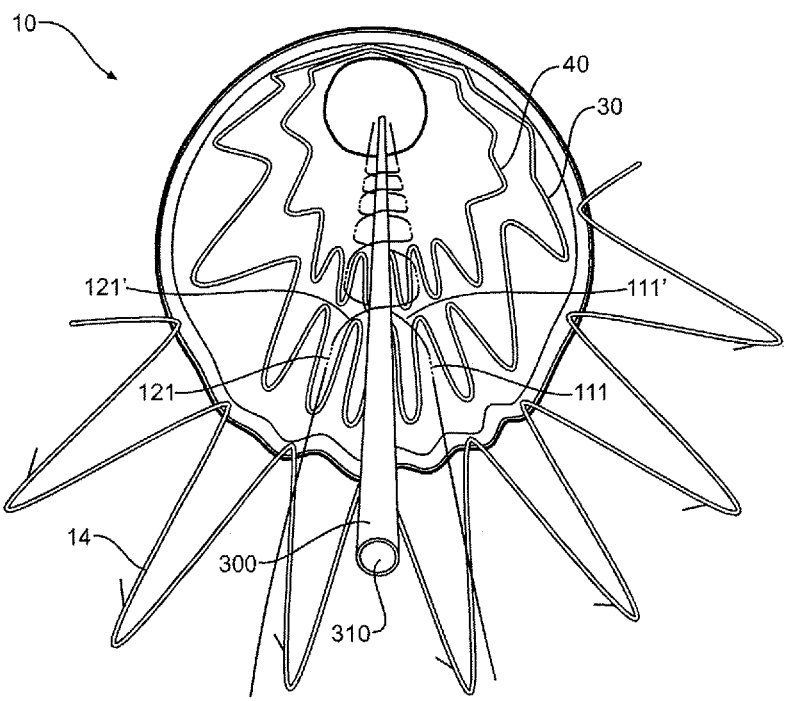
FIG. 4 is a perspective end view of the constraint arrangements shown in FIGS. 2 and 3 looking in from a proximal end thereof.
Figure 5:
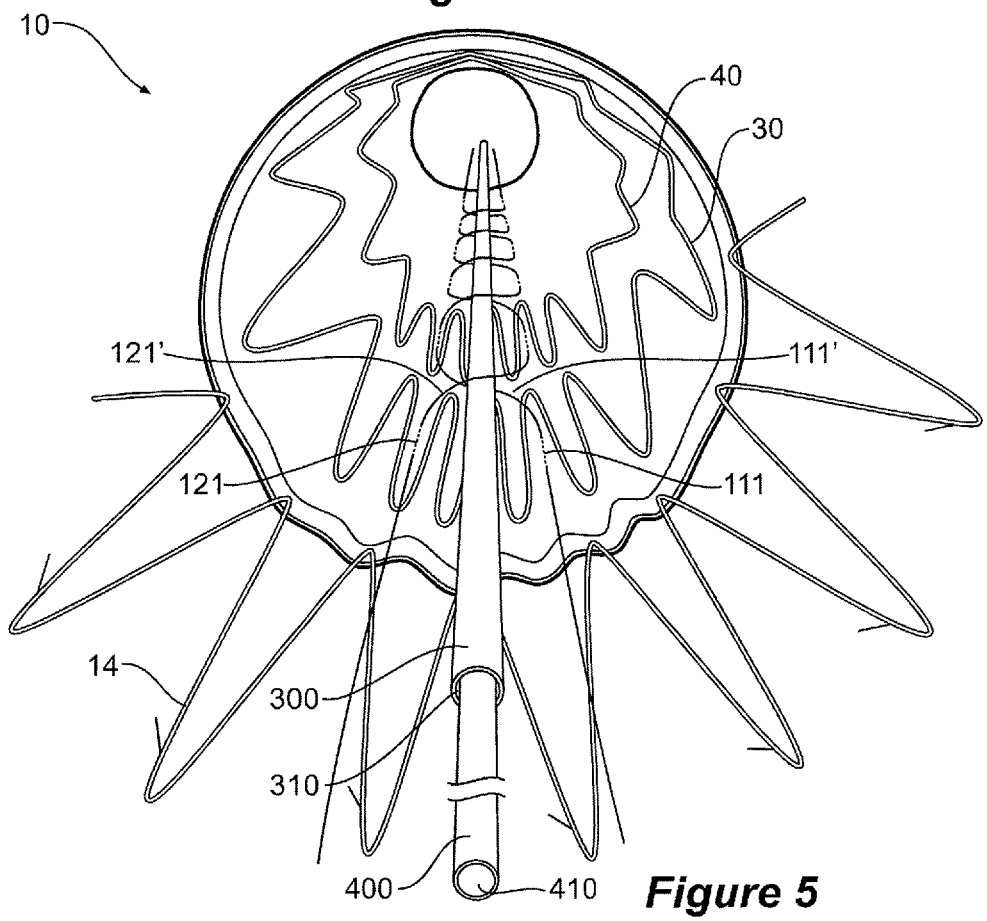
FIG. 5 is a similar view to that of FIG. 4, over a guide wire cannula of a delivery device.

As can be seen in FIGS. 4 and 5, the wires 110, 120 are arranged to sit on opposite sides of the receiver 300. This reduces wire to wire contact. Wire contact can be undesirable in some instances as it can potentially increase the chances of the creation on wire damage, shavings or entanglement.

The first and second wires 110,120 repeatedly penetrate a tubular wall 22 of the graft material tube 20 from inside the graft material tube 20 to outside the graft material tube 20 and then penetrate the tubular wall 22 back from outside the graft material tube 20 to inside the graft material tube, thereby forming a plurality of external wire portions including portions 124 and 114 shown in FIG. 2. Wire 110, as a result of the repeated penetrations just described, creates external wire portions 111, 112, 113, 114, 115, 116 and 117. Similarly, wire 120 forms external wire portions 121, 122, 123, 124, 125, 126 and 127.

The stents of the embodiments of the invention may have any suitable stent pattern known in the art. The stents may be balloon expandable. Preferably, the stents may be self-expandable. The stents can maintain the patency of the prosthesis and ensure adequate sealing against the surrounding vascular tissue. One goal for stent design and placement, whether internal or external, may be to prevent metal-to-metal contact points, prevent contact between two different types of alloys, and minimize micromotion. Stent sizing, spacing, and design may be determined so that there is no stent-to-stent contact even in tortuous anatomy. Stents preferably may be placed to maximize prosthesis flexibility while maintaining patency, as well as reduce material wear and stent fatigue. Furthermore, it is preferable that the stents do not interfere with the branch, that they minimize the potential for galvanic corrosion, and ensure adequate joint stability. Stent amplitude, spacing, and stagger preferably may be optimized for each prosthesis design. Any of the stents mentioned herein may have barbs and/or other anchoring members to help decrease prosthesis migration.

One example of a stent pattern is the Z-stent or Gianturco stent design. Each Z-stent may include a series of substantially straight segments or struts interconnected by a series of bent segments or bends. The bent segments may include acute bends or apices. The Z-stents are arranged in a zigzag configuration in which the straight segments are set at angles relative to one another and are connected by the bent segments. This design provides both significant radial force as well as longitudinal support. In tortuous anatomy, branches, or fenestrations, it may be preferable to use alternative stents or modifications to the Z-stent design to avoid stent-to-stent contact. Alternative stents may include, for example, annular or helical stents. Furthermore, in complex anatomical situations, external stents may have the potential to become intertwined with the wires or other devices utilized to ensure branch vessel access, sealing, and fixation. Thus, in some instances, it may be desirable to affix some of the stents to the internal surface of the prosthesis.

The stents described herein may be made from any suitable material known in the art. In one example, the stents may be made from standard medical grade stainless steel and are soldered using silver standard solder (0 lead/0 tin). In other examples, the stents may be made from a metallic material selected from any type of stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, a molybdenum alloy including about 0.4% to about 0.8% of lanthanum oxide ($Li_2O_3$), and a nickel-titanium alloy, or other suitable materials known in the art. The stents also may be made from nitinol or other shape-memory metal. Moreover, the stents may be configured in a variety of ways to provide a suitable intraluminal support structure. For example, one or more stents may be made from a woven wire structure, a laser-cut cannula, individual interconnected rings, or another pattern or design.

It can be seen from FIGS. 2, 3, 4 and 5 that the stents are zig-zag stents comprising struts and bends. For instance, referring to FIG. 2, an intermediate stent 50 (an external stent) including struts 51, 53, 55, 57, 59 can be seen. Additional struts are also part of the stent 50 but are not visible in FIG. 2. The stent 50 also has bends including bends 52, 54, 56, and 58. These struts and bends form peaks and valleys. The intermediate stents (those stents between the end stents), including stents 50 and 60, are longitudinally spaced apart such that their respective peaks are substantially aligned, as can be seen in FIGS. 2 and 3. For example, referring to FIG. 2, it can be seen that respective peaks 62, 66 of stent 60 are aligned with respective peaks 52,56 of stent 50.

Again referring to FIG. 2, it can be seen that the external wire portions are disposed within a V or an inverted V, formed between adjacent struts of one of the plurality of intermediate stents. For instance, external wire portion 113 is disposed within the inverted V formed between adjacent struts 53 and 55 of the intermediate stent 50.

Referring now to FIG. 5, the elongate receiver 300 is in the form of a temporary receiver tube having a through-bore 310. FIG. 5 shows the constraint arrangement of FIGS. 2, 3 and 4 loaded on to a guide wire cannula 400 of a delivery device. Once in this position, the receiver tube 300 can be removed and discarded leaving the constraint arrangement shown in FIGS. 6A, 6B and 6C.

Figure 6A:
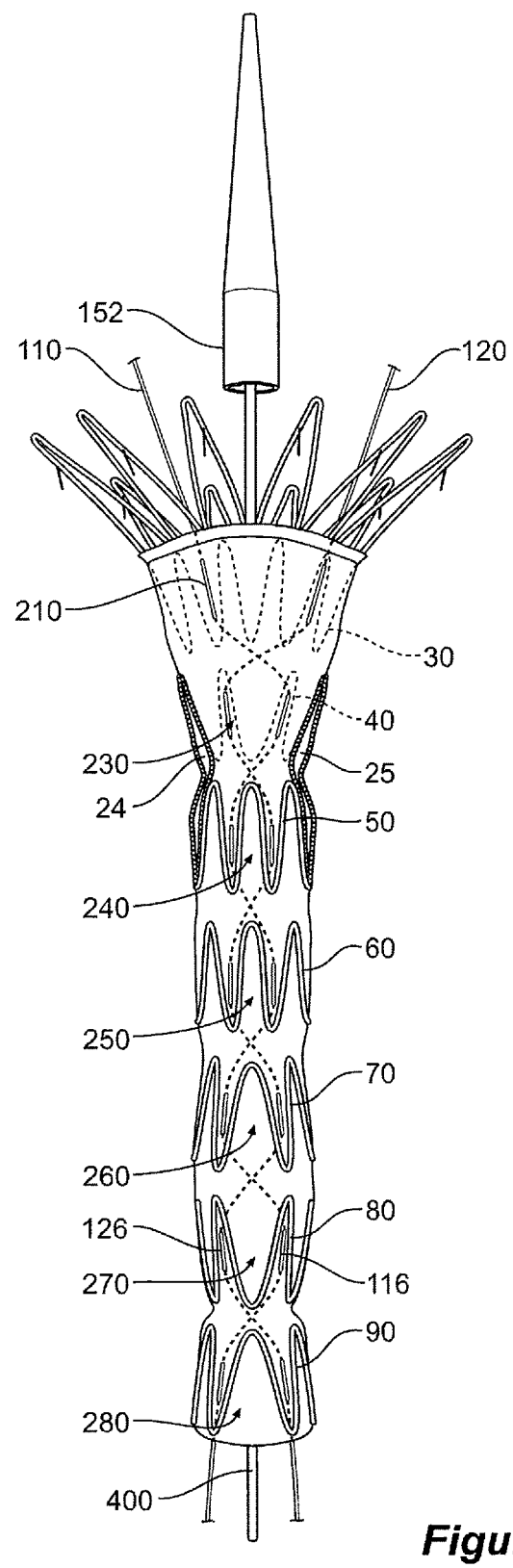

Embodiments of the invention may arise where no separate elongate receiver tube 300 is provided or required. With such embodiments, the constraint arrangement includes the guide wire cannula 400 of a delivery device as is shown in FIGS. 6A, 6B and 6C (instead of a temporary elongate receiver tube 300). However, in many applications it will be advantageous to use a disposable elongate receiver in the form of a temporary tube 300 as described above and as illustrated in FIGS. 2, 3 and 4.

In yet further embodiments of the invention, the temporary elongate receiving tube 300 may have a larger diameter than that shown in FIG. 5. With such embodiments, the internal bore 310 of the receiver tube may be sufficiently large to allow the constraint arrangement assembly shown in FIGS. 2, 3 and 4 to be slid over the top of a nose cone capsule 152 of the type illustrated in FIGS. 6A to 6C.

In yet further embodiments of the invention, the elongate receiver may be a stylet wire or other non-hollow member. With such embodiments, the elongate receiver would simply be a place marker for insertion of a guide wire cannula 400, such as the guide wire cannula 400 illustrated in Figure is 6A, 6B and 6C.

FIGS. 6A to 6C show a stent graft mounted onto a deployment device with a pusher catheter 150 at one end (see FIG. 6C) and a nose cone capsule 152 into which the proximally extending barbed stent 14 is received at the other end. In these drawings, no containing sheath is in place around the stent graft and so the stent graft is partially expanded under the influence of self expanding stents but complete expansion has been prevented by the wires 110 and 120.

The wires 110 and 120 can be removed by the surgeon when required. This will release the stent graft 10 from the guide wire catheter and will also allow stent graft 10 to expand under the action of the stents. This can be done when the stent graft is still mounted onto the deployment device so that the exposed stent 124 is still received in the capsule 152.

Figure 7:
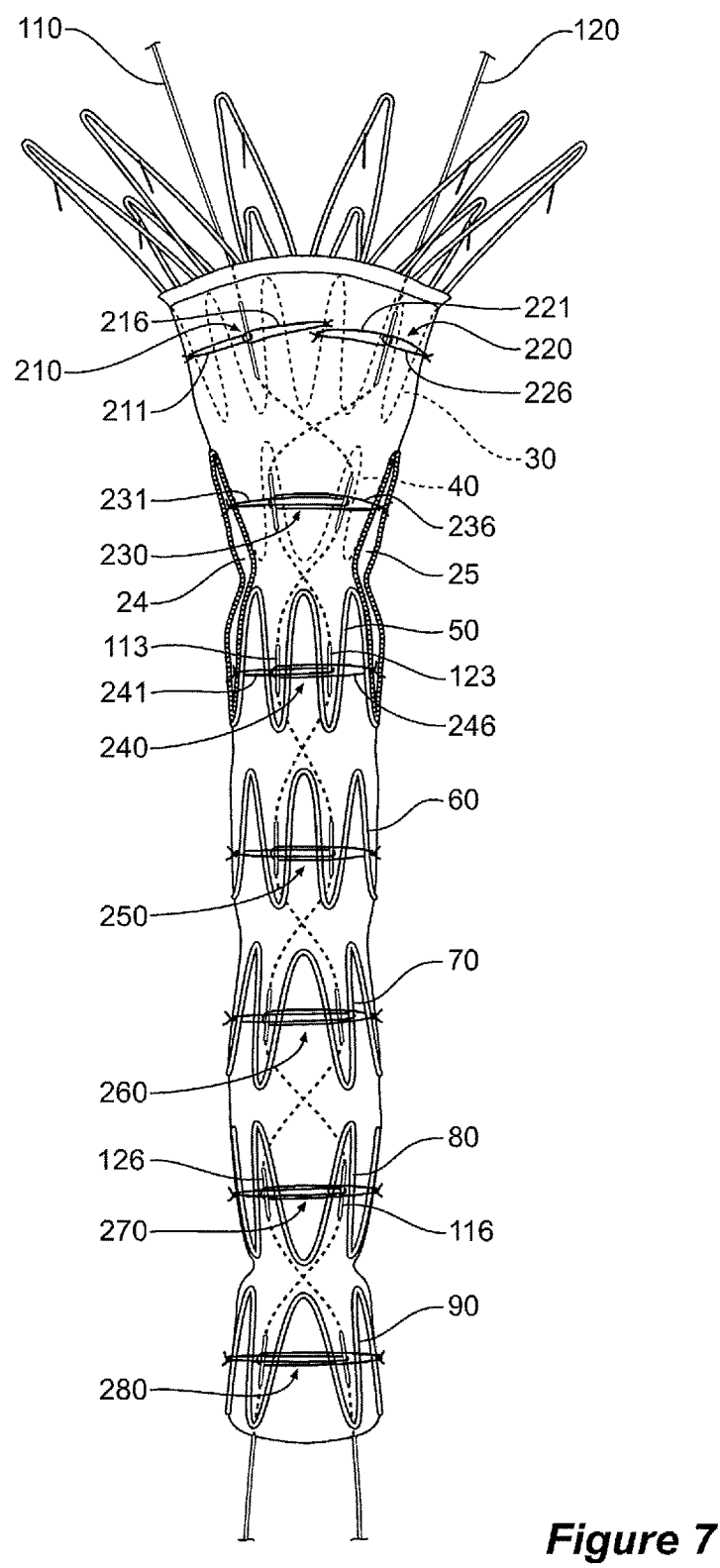
FIG. 7 shows an embodiment of the invention similar to that shown in FIG. 3 but having diameter reducing ties or sutures.

Now referring to FIG. 7, an embodiment of the invention similar to that shown in FIG. 3, but having diameter reducing ties or sutures is shown. A plurality of loops of thread, each loop engaged with one or other of the first and second wires and engaged around a portion of the stent graft circumferentially spaced a selected distance away from its wire, and drawn tight and tied to itself to reduce the stent graft.

The plurality of loops of thread are arranged in pairs and engage with one or other of the first and second wires 110,120 and engage around the portion of the stent graft circumferentially spaced a selected distance away from its wire. For instance, an end constraint arrangement comprising four loops of thread arranged into a first pair 210 and second pair 220 of threads (sutures) is provided, as can be seen in FIG. 7. The first pair 210 is engaged with the first wire 110 and the second pair 220 is engaged with the second wire 120, as is shown in FIG. 7. The first pair of threads 210 comprises a first thread 211 and a second thread 216. The second pair of threads 220 comprises a third thread 221 and a fourth thread 226.

Still referring to FIG. 7, an intermediate constraint arrangement comprising a fifth and sixth loops of thread 231 and 236 arranged in a third pair 230.

Figure 8A:
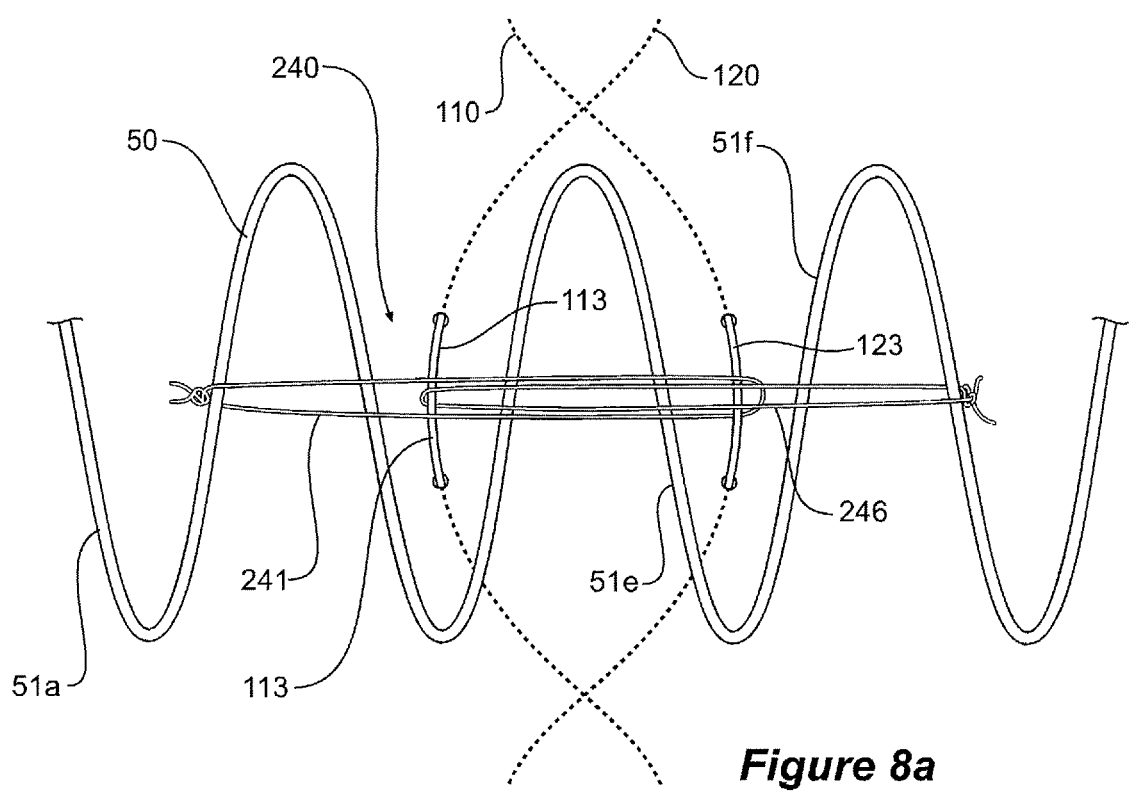
FIGS. 8A and 8B are detailed views showing the sutures or ties of FIG. 7 in an initial expanded condition and in a constrained or reduced condition respectively.
Figure 8B:
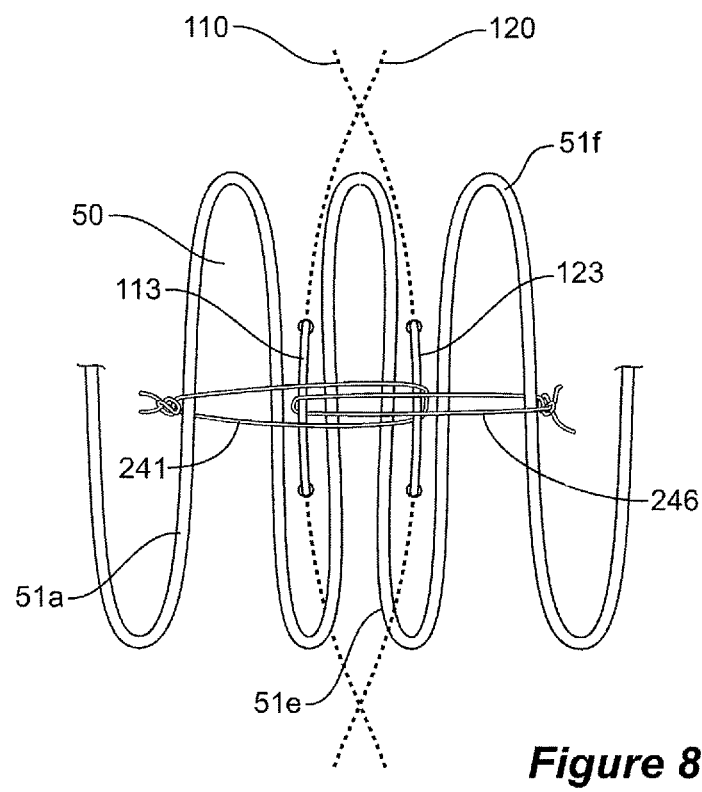

FIGS. 8A and 8B are detailed views showing the sutures or ties of FIG. 7 in an initial expanded condition and in a constrained or reduced condition respectively. Seventh and eighth loops of thread 241 and 246 arranged in a forth pair 240 is shown in FIGS. 8A and 8B.

Figure 9:
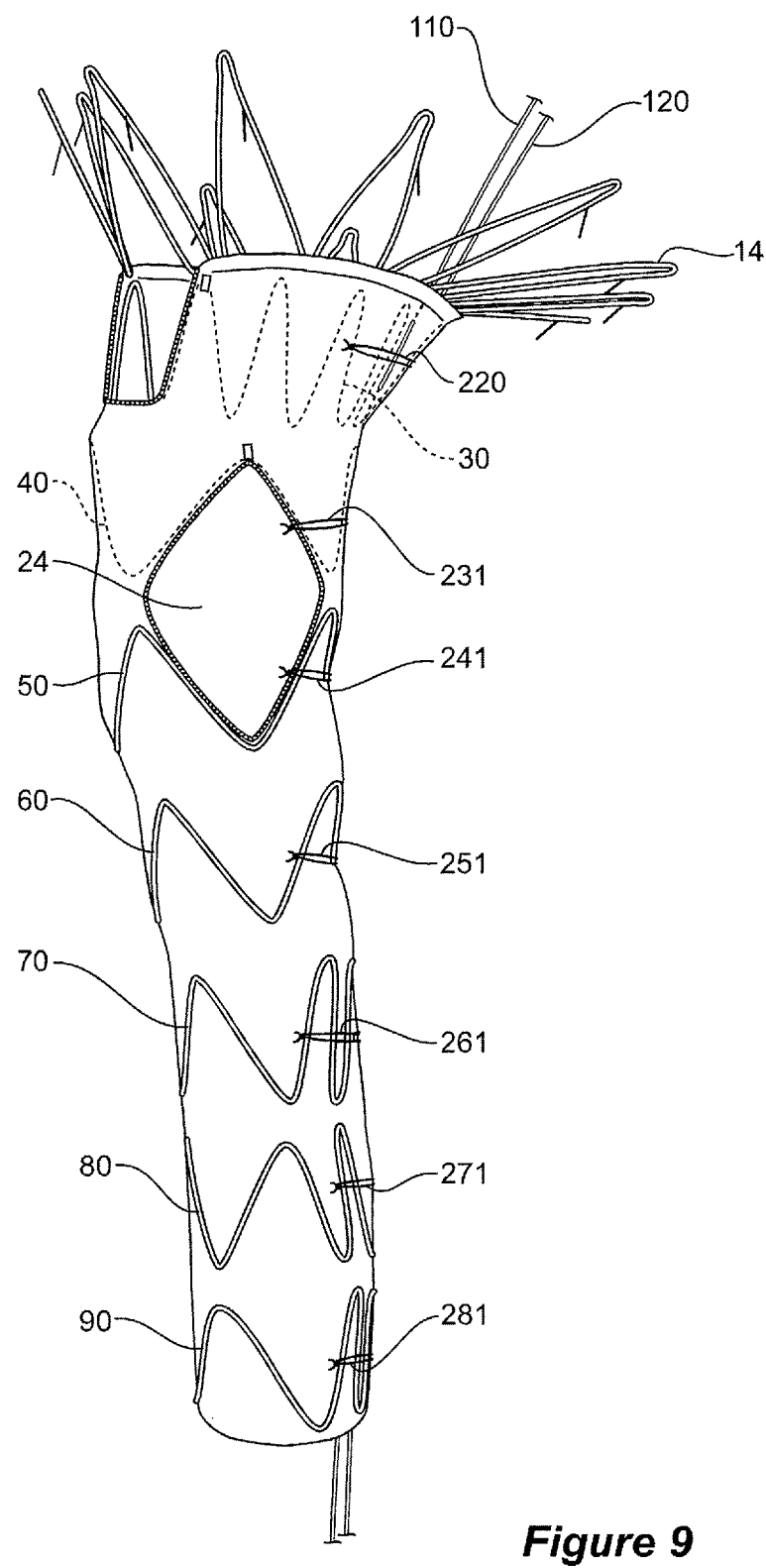
FIG. 9 is an isometric side view showing the constraint arrangement of FIG. 7 in a side view.

FIG. 9 is an isometric side view showing the constraint arrangement of FIG. 7 in a side view. This view also shows optional fenestrations 24 and 25 which can be provided for allowing access to the renal arteries as discussed previously above. This view also shows the first thread 211 of the first pair 210 of threads (sutures). It also shows the fifth, seventh, ninth, eleventh, thirteenth and fifteenth threads, 231, 241, 251, 261, 271, 281.

Figure 10:
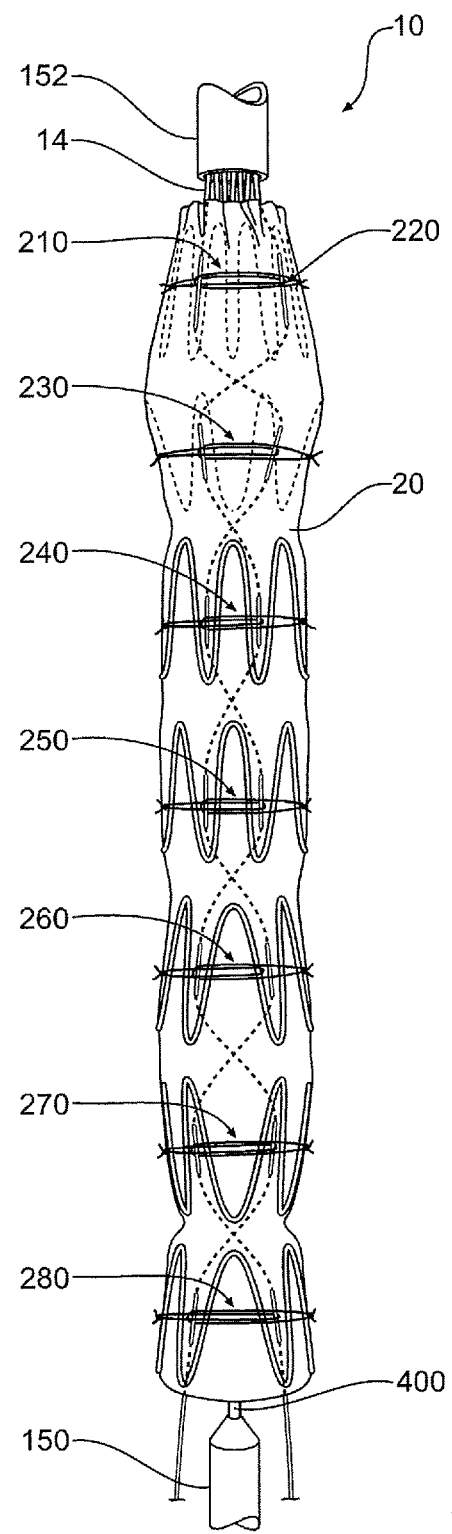
FIG. 10 shows an embodiment of the invention as part of a delivery device.

FIG. 10 shows the constraint arrangement of FIG. 7 as part of a delivery device. FIG. 10 is similar to FIG. 6C, but shows the stent graft of FIG. 7 mounted onto a deployment device with a pusher catheter 150 at one end and a nose cone capsule 152 into which the proximally extending barbed stent 14 is received at the other end. In these drawings, no containing sheath is in place around the stent graft and so the stent graft is partially expanded under the influence of self expanding stents but complete expansion has been prevented by the wires 110 and 120 and diameter reducing ties pairs 210, 220, 230, 240, 250, 260, 270 and 280.

The wires 110 and 120 can be removed by the surgeon when required. This will release the stent graft 10 from the guide wire catheter while at the same time will release the diameter reducing ties or sutures. This will also allow the stent graft 10 to expand under the action of the stents. This can be done when the stent graft is still mounted onto the deployment device so that the exposed stent 124 is still received in the capsule 152.

After removal of the wires 110 and 120, the sutures of the reducing tie pairs are released, but can remain on the outside of the stent graft. This does not cause problems as they do not interfere with blood flow and may assist with adhesion of the stent graft onto the wall of the aorta.

With the suture arrangement shown in FIGS. 7, 8A and 8B, labour is minimised. The arrangement also reduces the likelihood of the ties not releasing correctly due to incorrect sewing or other factors. This is important because, if fabric is caught, then this is likely to inhibit deployment of the stent graft within a lumen.

Figure 11:
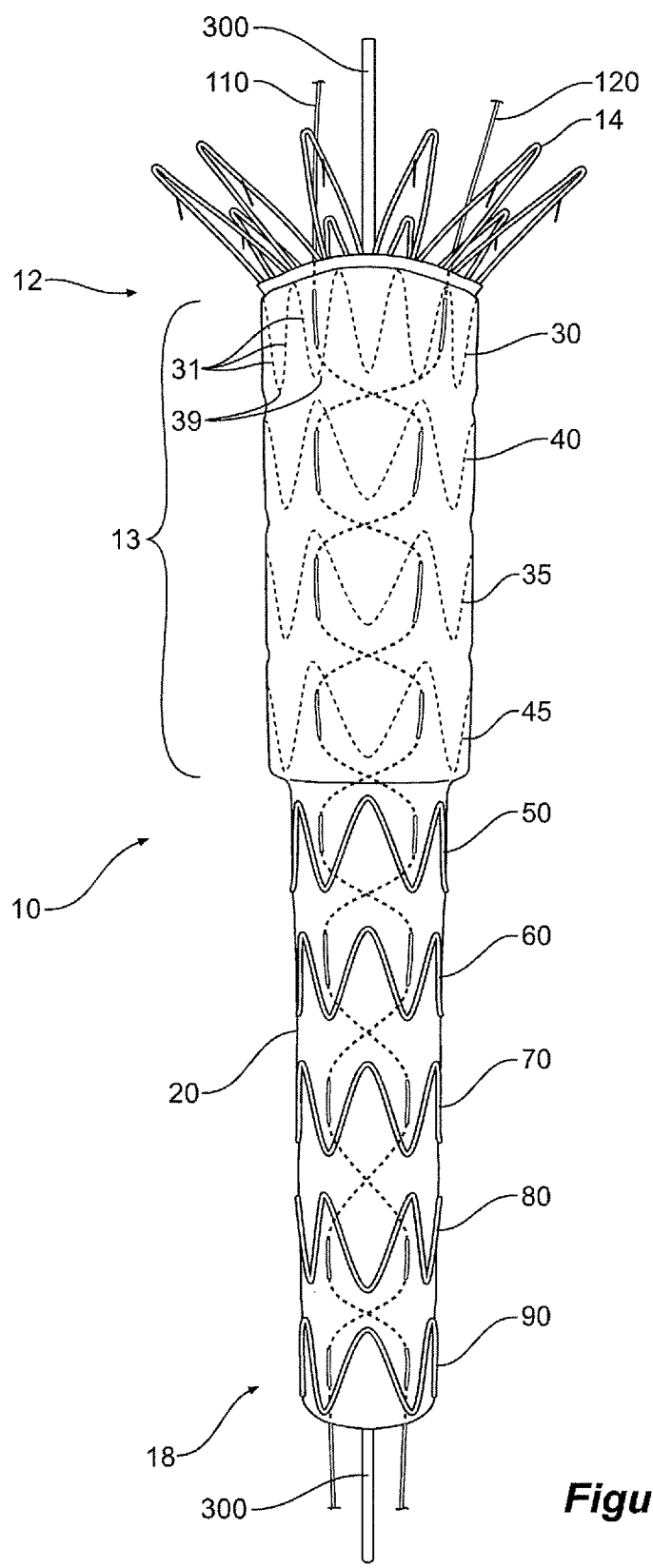
FIG. 11 shows a further alternative embodiment of the invention in an isometric view.

FIG. 11 shows a further alternative embodiment of the invention in an isometric view. This embodiment has a longer sealing zone 13. Other embodiments of the invention, not shown, will include stent grafts of differing shapes and sizes with and without fenestrations, bifurcations and other features.

With the embodiments illustrated, the expandable external stents 50, 60, 70, 80, 90 are nitinol (metal alloy of nickel and titanium) whereas the internal stents 30,40 are stainless steel. Nitinol is super-elastic and stainless-steel is non-super elastic. In other embodiments, other suitable materials may be used.

With the embodiments illustrated, the wires 110,120 are 0.014" Nitinol wires. Other wire diameters and other suitable materials may be used that are functionally similar to the wires illustrated and described above.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A temporary diameter reduction constraint arrangement for a stent graft in combination with a stent graft, the stent graft having a proximal end and a distal end, and an inner lumen between the proximal end and the distal end, a biocompatible graft material tube and a plurality of longitudinally spaced apart self-expanding stents fastened thereto, including at least an end stent and a plurality of intermediate stents, the constraint arrangement comprising:
   an elongate receiver extending longitudinally within the graft material tube;
   a first wire extending longitudinally along only a first side of the graft material tube in a first undulating serpentine pattern; and
   a second wire extending longitudinally along the first side of the graft material tube in a second undulating serpentine pattern opposite the first serpentine pattern, the first and second wires repeatedly penetrating the graft material tube from inside the graft material tube to outside the graft material tube and then penetrating the tubular wall back from outside the graft material tube to inside the graft material tube, where the first and second wires are configured to be tensioned to at least partially reduce the diameter of the stent graft, and
   wherein at least one of the first and second wires repeatedly loops over the elongate receiver along a longitudinal length of the stent graft to secure the stent graft to the elongate receiver along an internal wall of the stent graft.

2. The constraint arrangement of claim 1 wherein the first and second serpentine patterns cross each other in a criss-cross lacing pattern without extending about a circumference of the graft.

3. The constraint arrangement of claim 1 wherein the first and second wires repeatedly cross each other within the lumen of the graft material tube at intersection points disposed linearly along a longitudinally length of the stent graft.

4. The constraint arrangement of claim 1 wherein the first and second wires lie predominately inside the graft material tube.

5. The constraint arrangement of claim 1 wherein each intermediate stent is a zig-zag stent comprising struts and bends forming peaks and valleys and wherein the intermediate stents are longitudinally spaced apart such that their respective peaks are substantially longitudinally aligned.

6. The constraint arrangement of claim 1 wherein the elongate receiver is a temporary loading member, the temporary member provided to facilitate loading of the constraint arrangement onto a guide wire cannula.

7. The constraint arrangement of claim 6 wherein the temporary loading member comprises a tube having a through-bore.

8. The constraint arrangement of claim 1 wherein the elongate receiver is a guide wire cannula.

9. The constraint arrangement of claim 1, wherein the first and second undulating patterns each comprise a series of generally half-circles or half-ovals made alternately to the right and left.

10. The constraint arrangement of claim 9, wherein the series of generally half circles or half-ovals of the first serpentine pattern and the series of generally half circles or half-ovals of the second serpentine pattern form a series of generally full circles or full ovals extending longitudinally along the first side of the graft material tube.

11. The constraint arrangement of claim 1, wherein the first and second undulating patterns cross over each other in a criss-cross lacing pattern only on the first side of the graft material tube and within the lumen of the graft material tube.

12. The constraint arrangement of claim 11, wherein the first undulating serpentine pattern and the second undulating serpentine pattern criss-cross each other within the inner lumen.

13. The constraint arrangement of claim 11, wherein the first undulating serpentine pattern and the second undulating serpentine pattern criss-cross each other between adjacent stents of the plurality of intermediate stents.

14. The constraint arrangement of claim 1, wherein the first undulating serpentine pattern and the second undulating serpentine pattern criss-cross each other along the length of the stent graft at a plurality of intersection points, wherein the intersection points cross the elongate receiver within the lumen.

15. A temporary diameter reduction constraint arrangement for a stent graft in combination with a stent graft, the stent graft having a proximal end and a distal end and comprising a biocompatible graft material tube and a plurality of longitudinally spaced apart self-expanding stents fastened thereto, including at least an end stent and a plurality of intermediate stents, the constraint arrangement comprising:
  an elongate receiver extending longitudinally within the graft material tube;
  a first wire extending longitudinally along the graft material tube in a first longitudinally undulating pattern of successive curves in alternate directions;
  a second wire extending longitudinally along the graft material tube in a second longitudinally undulating pattern with successive curves in alternate directions opposite the successive curves of the first wire, the first and second wires repeatedly penetrating a tubular wall of the graft material tube from inside the graft material tube to outside the graft material tube and then penetrating the tubular wall back from outside the graft material tube to inside the graft material tube; and
  a plurality of loops of thread, each loop engaged with one or other of the first and second wires and engaged around a portion of the stent graft circumferentially spaced a selected distance away from the one or other of the first and second wires with which it is engaged, and drawn tight and tied to itself to reduce the stent graft, thereby securing the circumferential segment of the biocompatible graft material of the stent graft to the elongate receiver at multiple longitudinally spaced apart locations along a length of the graft material tube, while allowing partial expansion of the stent graft under the influence of the self expanding stents.

16. The constraint arrangement of claim 15 wherein the first and second undulating patterns cross each other in a criss-cross lacing pattern.

17. The constraint arrangement of claim 15 wherein the first and second wires repeatedly cross each other within the graft material tube.

18. The constraint arrangement of claim 17 wherein the first and second wires lie predominately inside the graft material tube.

19. The constraint arrangement of claim 15 wherein each intermediate stent is a zig-zag stent comprising struts and bends forming peaks and valleys and wherein the intermediate stents are longitudinally spaced apart such that their respective peaks are substantially longitudinally aligned.

20. The constraint arrangement of claim 15 wherein the elongate receiver is a temporary loading member, the temporary member provided to facilitate loading of the constraint arrangement onto a guide wire cannula.

21. The constraint arrangement of claim 20 wherein the temporary loading member comprises a tube having a through-bore.

22. The constraint arrangement of claim 15 wherein the elongate receiver is a guide wire cannula.

23. A temporary diameter reduction constraint arrangement for a stent graft in combination with a stent graft, the stent graft having a proximal end and a distal end, and an inner lumen between the proximal end and the distal end, a biocompatible graft material tube and a plurality of longitudinally spaced apart self-expanding stents fastened thereto, including at least an end stent and a plurality of intermediate stents, each intermediate stent being a zig-zag stent comprising struts and bends forming peaks and valleys, the intermediate stents longitudinally spaced apart such that their respective peaks are substantially longitudinally aligned, the constraint arrangement comprising:
  an elongate receiver extending longitudinally within the graft material tube,
  the elongate receiver comprising a tube having a through-bore;
  a first wire extending longitudinally along the graft material tube in a first longitudinally undulating pattern;
  a second wire extending longitudinally along the graft material tube in a second longitudinally undulating pattern opposite the first longitudinally undulating pattern, the first and second undulating patterns crossing each other in a criss-cross lacing pattern, the first and second wires repeatedly penetrating a tubular wall of the graft material tube from inside the graft material tube to outside the graft material tube and then penetrating the tubular wall back from outside the graft material tube to inside the graft material tube; and
  a plurality of loops of thread, each loop engaged with one or other of the first and second wires and engaged around a portion of the stent graft circumferentially spaced a selected distance away from the one or other of the first and second wires with which it is engaged, and drawn tight and tied to itself to reduce the stent graft,
  wherein at least one of the first and second wires repeatedly loops over the elongate receiver along a longitudinal length of the stent graft within the lumen of the stent graft to secure the stent graft to the receiver along an internal wall of the stent graft at multiple longitudinally spaced apart locations along a length of the graft material tube, while allowing partial expansion of the stent graft under the influence of the self-expanding stents, the first and second wires repeatedly crossing each other within the graft material tube and the first and second wires lying predominately inside the graft material tube.

24. A temporary diameter reduction system for a stent graft comprising:
  a stent graft having a proximal end, a distal end, an internal lumen between the proximal end and the distal end, a graft material tube, a graft material sidewall and a plurality longitudinally spaced apart self-expanding stents attached to the graft material sidewall and including at least an end stent and a plurality of intermediate stents;

a guidewire catheter extending longitudinally through the lumen of the stent graft;

a first wire extending longitudinally along only a first side of the graft material tube in a first undulating pattern of successive curves in alternate directions;

a second wire extending longitudinally along only the first side of the graft material tube in a second undulating pattern of successive curves in alternate directions opposite the first undulating pattern, the first and second wires repeatedly extending through the graft material sidewall from inside the graft material tube to outside the graft material tube such that a portion of at least one of the first and second wires extends over the guidewire catheter along a longitudinal length of the guidewire catheter to secure the guidewire catheter at least partially to an internal wall of the stent graft.

25. A temporary system for a securing a stent graft to a catheter of a stent graft delivery system comprising:

a stent graft having a proximal end, a distal end, an internal lumen between the proximal end and the distal end, a graft material tube, a graft material sidewall and a plurality longitudinally spaced apart self-expanding stents attached to the graft material sidewall and including at least an end and a plurality of intermediate stents;

a guidewire catheter extending longitudinally through the lumen of the stent graft;

a first wire extending longitudinally along only a first side of the graft material tube in a first undulating pattern of successive curves in alternate directions, the first wire repeatedly extending through the graft material sidewall from inside the graft material tube to outside the graft material tube such that a portion of the first wire extends over the guidewire catheter along a longitudinal length of the guidewire catheter to secure the guidewire catheter at least partially to an internal wall of the stent graft.

26. The temporary system of claim 25 further comprising a second wire extending longitudinally along only a first side of the graft material tube in a second undulating pattern of successive curves in alternate directions opposite the first undulating pattern.

27. The temporary system of claim 26, wherein the first undulating pattern comprises a series of generally half-circles or half ovals made alternately to the right and left.

28. The temporary system of claim 27, wherein the second undulating pattern comprises a series of generally half-circles or half ovals made alternately to the right and left.

29. The temporary system of claim 28, wherein the series of generally half circles or half ovals of the first undulating pattern and the series of generally half circles or half ovals of the second undulating pattern form a series of generally full circles or full ovals extending longitudinally along the first side of the graft material tube.

30. The temporary system of claim 26, wherein the first and second undulating patterns cross over each other in a criss-cross lacing pattern only on the first side of the graft material tube and within the lumen of the graft material tube.

31. The temporary system of claim 26, wherein the first undulating pattern and the second undulating pattern criss-cross each other within the inner lumen and over the guidewire catheter.

32. The constraint arrangement for a stent graft of claim 23, wherein the first longitudinally undulating pattern and the second longitudinally undulating pattern criss-cross each other between adjacent stents of the plurality of intermediate stents.

33. The constraint arrangement for a stent graft of claim 1, wherein the first undulating pattern and the second undulating pattern criss-cross each other along the length of the stent graft at a plurality of intersection points, wherein the intersection points cross the elongate receiver within the lumen.

* * * * *

UNITED STATES PATENT AND TRADEMARK OFFICE
CERTIFICATE OF CORRECTION

PATENT NO. : 11,191,632 B2
APPLICATION NO. : 15/347907
DATED : December 7, 2021
INVENTOR(S) : Chantelle King et al.

It is certified that error appears in the above-identified patent and that said Letters Patent is hereby corrected as shown below:

In the Claims

Column 10, Claim 1, Line 30, delete "," and replace with --;--.

Column 10, Claim 9, Line 63, after "undulating", insert --serpentine--.

Column 11, Claim 11, Line 6, after "undulating", insert --serpentine--.

Column 12, Claim 23, Line 53, after "stent graft to the", insert --elongate--.

Column 14, Claim 30, Line 20, delete "claim 26" and insert --claim 27--.

Column 14, Claim 33, Lines 33-34, delete "claim 1" and insert --claim 26--.

Signed and Sealed this
Twenty-fourth Day of May, 2022

Katherine Kelly Vidal
*Director of the United States Patent and Trademark Office*